United States Patent
Keating et al.

(10) Patent No.: US 6,503,755 B1
(45) Date of Patent: Jan. 7, 2003

(54) PARTICLE TRANSFECTION: RAPID AND EFFICIENT TRANSFER OF POLYNUCLEOTIDE MOLECULES INTO CELLS

(75) Inventors: Armand Keating, 71 Harper Avenue, Toronto, Ontario, M4T 2L4 (CA); Kathryn E. Matthews, Etobicoke (CA); Gordon B. Mills, Scarborough (CA)

(73) Assignee: Armand Keating, Ontario (CA)

( * ) Notice: Subject to any disclaimer, the term of this patent is extended or adjusted under 35 U.S.C. 154(b) by 0 days.

(21) Appl. No.: 07/959,317

(22) Filed: Oct. 13, 1992

(51) Int. Cl.$^7$ ............................ C12P 21/06; C12P 15/00; C07K 16/00; C07H 21/02
(52) U.S. Cl. .................... 435/455; 435/6; 435/69.1; 435/320.1; 435/325; 435/468; 435/471; 530/387.1; 530/388; 530/388.2; 530/389.2; 536/23.1
(58) Field of Search ......................... 435/6, 7.1, 7.21, 435/69.1, 172.3, 240.1, 240.54, 252.3, 240.23, 240.24, 240.243, 320.1, 325, 455, 468, 471; 501/11, 33; 530/387.1, 388, 388.2, 389.2

(56) References Cited

PUBLICATIONS

Sambrook, et al. 1989. in "Molecular Cloning: A Laboratory Manual, 2$^{nd}$ Ed.", Cold Spring Harbor Laboratory Press, N.Y. p. 16.30.*
"Introduction of DNA in Mammalian Cells" in *Current Protocols in Molecular Biology*, Ausubiel et al., Eds. 1988. John Wiley & Son, N.Y., pp. 9.0.1–9.5.4. Wysocki et al. 1978. Proc. Natl. Acad. Science, USA 75(6): 2844–2848.*
Kitigawa. et al. 1981. Control of Passive Permeability of Chinese Haneth Ovary Cells by External and Intracellular ATP, Biochem/Biophys ACTA 815 76–82.
Rozengeut et al. 1977. "Effect of Exogenous ATP on the Permeability Properties of Transformed Culture of Mouse Cell Lines" Proc. Natl Acad. Sci. USA 252 (13):4584–4590.
Mure et al. 1992. Jpn. J. Cancer Res. 83:121–126.
Kitigawa et al. $^{1983}$ Biochimica et Biophysica Acta 734:25–32.*
Thomas et al. 1987. Cell 51:503–512.*
Seed et al. 1987. Proc. Nat'l Acad Sci, USA. 84:3365–3369.*
Toneguzzo et al., *Nucl. Acid Res.* 16: 5515 (1988).
Fechheimer et al., *Proc. Nat'l Acad. Sci.* USA 84: 8463 (1987).
McNeil et al., *J. Cell Sci.* 88:669 (1987).
McNeil et al., *J. Cell Biol.* 98: 1566 (1984).
Facchini et al., *Biotech. and Bioeng.* 37: 387 (1991).
Facchini et al., *App. Microbiol. Biotech.* 33: 36 (1990).
Swanson et al., Methods in Molecular Biology, vol. 6, *Plant Cell and Tissue Culture* 159–169 (1990).
Hayashimoto et al., *Plant Physiol.* 93: 857 (1990).
Swanson et al., *Plant Cell Reports* 7: 83 (1987).
Asano et al., *Plant Science* 79: 247 (1991).
Swanson et al., *Theor. Appl. Genet.* 78:831 (1989).
Facchini et al., *Biomaterials* 10: 318 (1989).
Kaeppler et al., *Plant Cell* Reports 9: 415 (1990).

* cited by examiner

*Primary Examiner*—Scott D. Priebe
*Assistant Examiner*—Sumesh Kaushal
(74) *Attorney, Agent, or Firm*—Foley & Lardner

(57) ABSTRACT

A rapid, simple method of directly transfecting a large number of eukaryotic, prokaryotic or plant cells, which retains substantial cell viability is achieved by the present invention. The method includes the steps of contacting with cells adhered to a support, an amount of polynucleotide molecule targeted for transfection into the cells and an amount of particles. A gentle agitation of the cells, polynucleotide molecules and particles permits direct transfection of the polynucleotide molecules into the cells.

13 Claims, No Drawings

PARTICLE TRANSFECTION: RAPID AND EFFICIENT TRANSFER OF POLYNUCLEOTIDE MOLECULES INTO CELLS

BACKGROUND OF THE INVENTION

The present invention relates to method for transferring polynucleotide molecules into living cells by contacting the cells with small particles in the presence of a polynucleotide molecule-containing solution. The inventive method provides a rapid, simple procedure by which a large number of cells can be transfected with an efficiency comparable to that of existing transfection methods.

Gene transfer is an important technique in the genetic engineering of prokaryotic, eukaryotic and plant cells. Gene transfer has many applications, including for example, in human gene therapy, in the production of transgenic or genetically-improved livestock and plants, and in basic research.

Many physical methods have been described for the introduction of polynucleotide molecules into mammalian cells, including calcium phosphate co-precipitation, electric field-mediated gene transfer, direct microinjection, DEAE-dextran transfer, lipofection, fusion of erythrocytes or liposomes, osmotic lysis of pinosomes, centrifugation loading, and delivery of high velocity microprojectiles.

In the past decade, scientists have favored using a retrovirus to introduce exogenous genetic material into cells. In this method, a polynucleotide molecule or gene of interest to be transfected into a cell is first ligated within the genome of a retroviral vector. The retroviral vector containing the desired gene then uses the retrovirus's natural mechanism of infection to carry the gene into the cell. A disadvantage of this method is that the retroviral vector itself becomes an intracellular contaminant while carrying the target gene into the cell.

Three methods which directly introduce functional genetic material into living cells, and thereby avoid introducing extraneous viral genetic material into the cell, are electroporation, scrape-loading and bead loading. A common underlying mechanism between these methods is that each produces a transient disruption of the cell's plasma membrane, during which exogenous genetic molecules are able to diffuse inwardly.

Electroporation as described by Toneguzzo et al., *Nucl. Acid Res.* 16: 5515 (1988), provides a method for transfecting a large number of cells by delivering an electrical shock in order to temporarily disrupt membrane permeability. Although the electroporation method offers the advantage of direct DNA transfection into cells, there are several drawbacks to the method. Electroporation requires that a large number of cells be used, since 35–60% of the original number are killed by the electrical shock. Additionally, the electroporator machine is expensive, and the technique requires a minimum of about ½–2½ days to complete.

In the scrape-loading method of transfection, described by Fechheimer et al., *Proc. Nat'l Acad. Sci. USA* 84: 8463–67 (1987), a monolayer of cells adhered to a petri dish are contacted with a DNA loading solution. Next, the cells are loaded with DNA by gently scraping the cells with a blunted object. Scraped cells are removed from the petri dish and replated on another petri dish, grown in medium, and then assayed for gene expression.

In the scrape-loading method, replating the transfected cells takes one or two days, which is a serious disadvantage of the method. Consequently, the method cannot be used for investigations, for example, which utilize labels that degrade over such a lengthy time period. In addition, during scrape-loading, the cells undergo severe mechanical strain during the scraping action, which results in the loss of massive numbers of cells.

In achieving an analogous goal of loading molecules into living cells, the technique of "bead loading" described by McNeil et al., *J. Cell Sci.* 88: 669–77, (1987) was used. In this method, cells growing on a cover slip are exposed to a solution of macromolecules. Next, small glass beads are sprinkled over the surface of the cover slip, and gently rocked to evenly distribute the beads. The cover slips are washed, returned to culture medium, and examined for loading of the macromolecules.

Bead loading presents several advantages, including the ability to load large numbers of cells in only a few minutes time. Also, bead loading is performed on cells which are adhered to a surface, and does not require replating the cells after macromolecule loading. Bead loading of macromolecules causes less cell loss than does scrape-loading (McNeil et al., *J. Cell Biol.* 98: 1566–64 (1984). Thus, a method of transfecting polynucleotide molecules into cells which achieves many of the advantages offered by the bead loading technique for macromolecules is desired.

SUMMARY OF THE INVENTION

It is therefore an object of the present invention to provide a method for transfecting adherent cells with polynucleotide molecules in just a few minutes time.

It is a further object to provide a method for serially transfecting a large amount of cells by recycling a polynucleotide/buffer solution used to particle transfect a first set of cells to particle transfect additional cells.

It is another object of the invention to provide an approach to transfection which achieves an efficiency of transfection and which maintains cell viability at levels comparable to other transfection methods.

It is a further object of the invention to provide a means of introducing polynucleotide molecules directly into cells which is performed easily and inexpensively without the need for expensive machinery or laborious techniques.

It is another object of the invention to particle transfect mammalian, bacterial, or plant cells (including haploid cells, protoplasts and haploid protoplasts).

In accomplishing these and other objects, there has been provided, in accordance with one aspect of the present invention, a method for transfecting polynucleotide molecules into cells, comprising the steps of providing a quantity of cells adhered to a support, contacting the cells with an amount of polynucleotide molecule, contacting the cells with particles and imparting kinetic energy to the particles such that contact between particles and cells occurs, whereby the cells are transfected with polynucleotide molecule to create transfected cells. A further step of detecting transfected cells which express the polynucleotide molecule also is provided.

Another object of the invention is to provide a method for transfecting polynucleotide molecules into cells which includes a recycling step. After performing particle transfection on a first set of cells, recycling comprises the steps of removing polynucleotide/buffer solution from the particle-transfected cells and bringing the solution into contact with a second set of cells adhered to a support, and transfecting the second set of cells.

Yet another object of the invention is to provide a method of adhering non-adherent cells to be transfected to a support, such as by contacting non-adherent cells with a ligand capable of binding to a support and to non-adherent cells to be transfected, and then performing particle transfection.

Another object of the invention is to provide a kit for use in transfecting a polynucleotide molecule into non-adherent cells, comprising a first receptacle containing a quantity of sterilized particles for use in particle transfection of cells and a second receptacle containing dehydrated buffer A.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The present invention provides a rapid, inexpensive and efficient method for transfecting small or large-sized polynucleotide molecules into cells. A method within the present invention includes the steps of providing an amount of cells adhered to a support and bringing the cells into contact with an amount of particles and polynucleotide molecules in a buffer solution. Thereafter, agitating the cells and particles results in a transient cell membrane disruption which permits direct transfection of polynucleotide molecules into the cells.

Particle transfection is fast and simple to perform on cells already adhered to a support, i.e., adherent or plated cells. According to the present method, particle transfection of adherent cells takes less than about five minutes to perform (using pretreated particles as described herein).

The method achieves an advantage over the transfection method of scrape-loading, by providing a high viability of transfected cells and by avoiding a replating step, which is required after transfection the by scrape-loading method. According to the present method, after particle-transfection is performed, polynucleotide molecules and particles are removed, and the newly-particle-transfected cells are simply incubated for a period of 24–72 hours, preferably for 48–72 hours, in a suitable media, temperature, and atmosphere for promoting expression of the transfected polynucleotide and cell growth. Media, temperature and atmosphere conditions, in general, will be selected to promote growth of the type of cell being transfected.

Large amounts of cells are particle transfected according to the invention by serial transfection of several sets of cells at a time. Serial transfection is accomplished by removing the polynucleotide/buffer solution from a set of cells which was particle transfected by the above-described method. Removal is easily accomplished, for example, by siphoning the solution with a pipette. Next, the reclaimed solution is applied to a second set of cells to be particle transfected.

In this manner, large numbers of cells are quickly transfected, as illustrated by the following. A conventional-sized plate (petri dish) of cells containing about 2 million cells can be transfected pursuant to the invention within about 3 to 5 minutes. The polnucleotide/buffer solution then can be reclaimed and applied to a second plate, which is subsequently particle-transfected. This process can be repeated a multitude of times, resulting in particle transfection of about 10 million cells in about 15 minutes.

Other advantages achieved with the present method include both a transfer efficiency and a sustained cell viability level which are comparable to that of other transfection methods. Efficiency is determined by the following procedure. First, particle transfection is performed either in the presence or absence of polynucleotide molecule, such as a plasmid containing a selectable marker gene for antibiotic resistance. Cells are grown for a few weeks after transfection and assayed for stable integration, as indicated by survival under conditions selective for gene expression. Transfection efficiency is a ratio of the number of cells which survive under conditions selective for the transfected gene, relative to the number of cells surviving transfection but not surviving under the selective growing conditions.

A large number of cells which undergo particle transfection remain viable. A measurement of cell viability is obtained by particle transfecting a plate of cells in the presence or absence of polynucleotide molecules. The number of surviving transfected cells versus sham transfected cells is compared 4 hours after transfection. The average percentage of the number of original cells surviving is cell-type specific and was found to be about 57%±16%. The presence of concentrated DNA did not affect cell viability.

The advantages achieved by the present particle transfection method, in terms of time-savings, cost, transfection efficiency and cell viability can be illustrated by comparison to electroporation. The electroporation method, as described by Tonezuggo et al., *Nucl. Acid Res.* 16: 5515 (1988), requires a minimum of about 4 hours to transfect cells (see Example 10). Cells are then plated and incubated (similar to that of particle-transfected cells) for at least 24 to 72 hours.

The efficiency of particle transfection, as measured by transient expression, is about the same as that of electroporation. For performing the electroporation procedure, however, about 10 million cells are required per transfection experiment. Consequently, where an investigation requires that only a million cells be transfected, the electroporation method would require an initial dedication of time and resources devoted to increasing the cell population to a sufficient number before the method could be used. In contrast, a million cells can be particle transfected in about 3–5 minutes without a first step of growing up the cells.

Particle transfection also avoids expenses which accompany electroporation, including the costs of an electroporator machine and of the extensive cell loss which occurs in use of the method. The percentage of cell death with electroporation can range between 20 to 65% of a large population of cells, as discussed above. Particle transfection, as calculated to include raw materials and labor, costs $1.61 (U.S. dollars, 1992) per million cells targetted. In contrast, the same costs for electroporation, not including depreciation costs of an electroporator (about $3000.00 new), is $8.20.

Particle transfection according to the present invention, as compared to the DEAE dextran transfection, is quicker, more efficient and less expensive. The DEAE dextran method, described by Holter et al., *Exp. Cell Res.* 184: 546 (1989), requires a period of 230 minutes. By contrast, transfection according to the present invention takes about 5 minutes to perform.

Particle transfection also is more efficient compared to the DEAE-dextran method of gene transfer. In experiments using linearized DNA (the same number of cells was used in both instances) particle transfection ranged from about equal to about 1.5 times more efficient, as determined by transient CAT activity (see Example 11).

Particle transfection is less expensive than DEAE dextran transfection. Particle transfection costs $1.61 (U.S. dollars, 1992) as compared to $40.38 for DEAE transfection per million cells transfected.

The particle transfection method of the present invention includes an initial step of bringing adherent cells into contact with a physiologic buffer, and preferably, washing the cells at least once with this buffer. Physiologic buffered saline is a preferred buffer in this context.

Next, the physiologic buffer is removed and replaced with buffer A, absent MgATP, according to the invention. "Buffer A" contains 140 mM KCl, 10 mM HEPES (pH 7.25), 1 mM EDTA, 0.193 mM $CaCl_2$, 10 mM glucose and 1 mM $MgCl_2$, and optionally, 1 mM MgATP. Cells to be transfected are washed with buffer A without MgATP at least once, preferably twice. This buffer is then removed and replaced with a polynucleotide/buffer solution.

Polynucleotide molecules can be present in a minimal volume of buffer A with 1 mM MgATP, thus defining a "polynucleotide/buffer" solution. In a preferred embodiment of the invention, the particles are also present in this minimal volume of buffer A (with 1 mM MgATP). For present purposes, a suitable volume of polynucleotide/buffer solution is that which, where brought into contact with the cells, is sufficient to obtain an even spread of particles over the cells, while keeping the total volume (and thus the amount of polynucleotide molecules required) to a minimum.

The amount of polynucleotide molecule present can affect the efficiency of transfection. For efficient transfection, polynucleotide/buffer concentration is more than 25 μg/ml, and more preferably, is 50 μg/ml. The particles either may be present in the polynucleotide/buffer solution or the solution may be contacted with the cells prior to addition of the particles, without significant effect on efficiency.

Upon bringing cells adhered to a support into contact with particles and polynucleotide/buffer solution, kinetic energy is imparted to the particles such that contact between the particles and the cells occurs, resulting in transfection of the cells with polynucleotide molecule. Energy may be imparted to the particles by gently agitating the support upon which the cells are adhered, preferably for a time period of about ten seconds. The agitation is accomplished, for example, by tilting the support from side to side three times.

Agitation is performed until an even distribution of particles over the cells is reached. Gentle agitation is preferred because excessive movement of the system (of cells, particles and polynucleotide molecules) beyond the movements described decreases cell viability. After agitation, the particles and polynucleotide molecules are removed with a sufficient volume of buffer A/MgATP to wash the surface of the cells.

In the present context, the phrase "polynucleotide molecule" denotes any selected from a group of deoxyribonucleic acid molecules (DNA), including the following examples. DNA molecules transfected according to the present method include prokaryotic, eukaryotic, mitochondrial, plasmid, viral or chemically-modified DNA; a DNA molecule which when transcribed is an antisense RNA sequence; or a mixture of any of the foregoing molecules. A "chemically-modified" polynucleotide molecule can include DNA molecules which are covalently or otherwise chemically bonded to a moiety, such as label or genetic signal for specific expression. Examples of moieties useful for labelling purposes can include radioactive or fluorescent compounds, such as phosphate ($^{32}P$) sulfate ($^{35}S$) or ethidium bromide. Polynucleotide molecules which are modified as a signal for specific expression within a particular host can include methylated bases.

Useful for antisense purposes is a deoxyribonucleic acid molecule, which upon transfection into the cell is transcribed to produce an antisense RNA sequence. An "antisense RNA sequence" is a non-naturally occurring ribonucleic acid sequence complementary to a target messenger ribonucleic acid sequence that is translated by the cell.

In a preferred embodiment, a polynucleotide molecule comprises a gene which encodes a desired protein. In a more preferred embodiment, a polynucleotide molecule further comprises a gene and a regulatory sequence, such as a transcriptional promoter or enhancer sequence, that is specific for modulating expression of the desired protein. A polynucleotide molecule containing one or several open reading frames encoding one or more proteins, can be transfected, also. Preferred in this context is a single polynucleotide molecule which comprises both a desired gene and a reporter gene, whereby expression of the lattermost readily identifies cells as probable positive transfectants containing the desired gene.

Either small polynucleotide molecules consisting of a few bases or very large polynucleotides are transfected according to the invention. Preferably, polynucleotides are smaller than about 30 kilobases.

The conformation of polynucleotide molecule transfected into cells can include a single, double or triplex strand polynucleotide molecule, which can be linearized or supercoiled. In a preferred embodiment, the polynucleotide molecule is linearized. As illustrated in Example 6, use of linearized plasmid DNA can result in a slightly higher transfection efficiency, relative to supercoiled DNA. For the most part, however, the transfection efficiencies achieved via the present invention are similar, irrespective of molecule conformation.

The term "particles" in the context of the present invention denotes beads or fragments made of glass, metal, plastic, ceramic or other material which can be conformed into smooth, suitable-sized pieces. The size of the particles affects transfection efficiency. Preferably, particles are rounded glass beads ranging in diameter size from 150–500 μm, or more preferably between 300–500 μm. A more preferred embodiment of the invention employs 425 μm particles which, as shown in Example 7, provide a high transfection efficiency.

According to the present invention, particles are prepared for use in transfection by the following pretreatment regimen. First, the particles undergo separate washes with a strong acid and a strong alkali solution for about 8 to 12 hours each. Between the washes, the particles are rinsed repetitively with deionized water. The washes are followed by soaking the particles for a few hours time in a solution of a lower alkyl alcohol, and then rinsing with buffer A/MgATP. Representative solutions useful in pretreatment include HCl and isopropanol, although other strong acids, or alcohols can be used to provide similar results. Particles which have been pretreated can be sterilely stored in a solution of sterile buffer A without MgATP for several days, then autoclaved prior to use to ensure sterility.

The particles used according to the method of the invention can be reclaimed and reused by rinsing them off of particle transfected cells with buffer A/MgATP and collecting them. In the present transfection method, magnetic particles or glass-coated magnetic particles can be used to facilitate the reclamation step. The metal particles can range in diameter size from 150–500 μm (Advanced Magnetics, Cambridge Mass.) and are easily reclaimed by passing a magnet over the top of the cells to attract the particles.

Particles and polynucleotide molecules are contacted with cells which, according to the present invention, are adhered to a support. "Adherent" in this description means that the cells are growing on, or are otherwise immobilized on a support.

A "support" as used in the present context is a solid surface upon which cells can adhere themselves. Preferred examples of supports are a petri dish or a flask. Alternatively, a large glass tray or a small surface (e.g., a glass coverslip) is used to transfect larger, industrial scale or smaller populations of cells, respectively.

It is preferred that the cells are plated onto a support and incubated for 24 to 48 hours in an appropriate media and atmosphere prior to particle transfection. Preferably cell growth occurs in a monolayer formation. A support can contain about 0.5 to 10 million cells each, but both the size of the support and the quantity of cells can be either increased or decreased in scale.

According to the present invention, cells which can be transfected by particle transfection preferably include eukaryotic, prokaryotic or plant cells which possess the ability to adhere themselves to a solid media or other support. As shown in Table 5, both COS cells and passaged human bone marrow stromal cells are examples of successfully particle-transfected mammalian cell lines.

Cells which are not susceptible to plating on a culture or which do not normally adhere or grow well on a support can be transfected according to the invention. This type of "non-adherent" cell can be immobilized on a support by interaction with a ligand which is or can readily be affixed to a support. Suitable ligands include a commercially-available antibody or pair of antibodies, lectins, or an extracellular matrix.

A preferred ligand is an antibody pair, which are employed as follows. Non-adherent cells are contacted, under conditions sufficient for binding to occur, with an amount of a "first antibody" specific for binding the cells to be transfected. Next, the first antibody-bound cells are contacted with a "second antibody" which is bound to or capable of being bound to a support. The second antibody binds the first antibody with sufficient affinity so as to indirectly adhere the first antibody to a support.

By way of example, particle transfection is performed on a solution of non-adherent purified CD34+ stem cells (obtained from blood by using a CellPro Ceprate (Bothell, Wash.) selection column) according to the present method. Purified stem cells are bound to a support, for example by binding with an anti-CD34+ antibody which itself can be directly or indirectly bound to a support.

Indirect binding is accomplished in the following manner. A first antibody, mouse-anti-humanCD34+ (Coulter Immunology, Hialeah, Fla.), is contacted with a preparation containing human CD34+ stem cells, resulting in bound mouse-anti-humanCD34+ cells. A second antibody, goat anti-mouse IgG (Jackson ImmunoResearch Laboratories, Inc., West Grove, Pa.), which is immobilized on a support, is contacted with the bound mouse-anti-humanCD34+ cells in a manner sufficient to promote binding between the second and first antibodies. Thereafter, the stem cells are particle-transfected according to the method described above.

Particle-transfected stem cells can be washed and returned to the same patient from which they were purified, to treat immune deficiencies, hematopoietic diseases or to perform gene therapy.

To facilitate performance of the particle transfection method in non-adherent cells, a first kit is provided which comprises a set of three receptacles, each containing either a preparation of a first antibody having specificity for a cell to be transfected, a preparation of second antibody which can bind both to the first antibody and to a support, or a quantity of sterilized particles for use in transfecting cells which are adhered to a support by means of binding between the first and second antibodies. The kit may further comprise a fourth receptacle containing dehydrated buffer A.

To facilitate performance of the particle transfection method in adherent or non-adherent cells, a second kit is provided which comprises a first and a second receptacle containing sterilized particles or dehydrated buffer A, respectively.

Intact plant cells, haploid plant cells, protoplasts and haploid protopasts, collectively termed "plant-prototransfectants," also can be particle-transfected according to the invention. To perform the method, plant-prototransfectants are cultured and adhered to a support, as follows.

A culture or suspension of plant-prototransfectants, after incubation in a suitable growth-promoting media for 2 days to 2 weeks, is first adhered to a "plant-support". Suitable plant-supports for particle transfection can include inert materials which possess both a high surface free energy and large surface area, to provide maximal adhesion given the physiochemical surface properties of the particular cell-type to be transfected and its respective liquid media requirements. Examples of such supports can include a glass fiber matrix, a calcium alginate gel (Brodelius et al., *FEBS. Lett* 103:93 (1979)) or polyurethane foam matrix (Lindsey et al., *FEBS Lett.* 155:143 (1983)).

A preferred plant-cell support, a glass fiber matrix, and a method useful for adhering plant-prototransfects are described by Facchini et al., *Biotech. and Bioeng.* 37: 397 (1991), incorporated by reference herein in its entirety. The glass fiber matrix can also be coated with a variety of coatings to modulate surface tension. Facchini et al., *App. Microbiol. Biotech.* 33: 36 (1990).

Intact plant cells and haploid plant cells are adhered according to the method of Facchini et al., (1991) supra. Haploid plant cells, such as plant microspores, can be isolated according to the method described by Swanson et al., METHODS IN MOLECULAR BIOLOGY, Vol. 6, *Plant Cell and Tissue Culture* 159–169 (1990).

Protoplasts and haploid protoplasts are isolated by conventional methods, as described by Li et al., "General medium for efficient plant regeneration from rice protoplasts" *Plant Cell Reports* (1990), and Hayashimoto et al., *Plant Physiol.* 93: 857 (1990); and Swanson et al., *Plant Cell Reports* 7: 83 (1987), respectively. The protoplasts can be adhered according to the aforementioned Facchini method. The effectiveness of this method may be enhanced by the addition of an effective amount of a positive cation, such as $CaCl_2$ or poly-1-lysine, to the cell suspension or culture to thereby promote adhesion of the negatively-charged protoplasts.

Preferably, plant prototransfectants are permitted to adhere to the plant cell support for at least 8 hours, more preferably between 24–60 hours. Next, the prototransfectants are washed with distilled water and a solution of polynucleotide molecule is added at an effective concentration within the range of 10–250 $\mu$g/ml. The polynucleotide molecule in this context is preferably a linearized or supercoiled plasmid DNA. Such plasmid DNA can contain the desired gene to be transfected, and a promoter or enhancer region, as well as a reporter gene, such as a β-glucuronidase (GUS) or neomycin phosphotransferase II (NPT II).

The particle transfection method is performed in a similar manner as described above with mammalian cells. The previously described particles either may be present in the polynucleotide solution or the solution may be contacted with the plant-prototransfectants prior to addition of the particles. Upon bringing plant-prototransfectants adhered to a plant-support into contact with particles and polynucleotide solution, kinetic energy is imparted to the particles such that contact between the particles and the cells occurs, resulting in transfection of the prototransfectants with polynucleotide molecule.

Thereafter, the plant transfectants are washed with distilled water, and incubated in appropriate fresh media, temperature and atmosphere for the cell-type being transfected. Preferably, the plant transfectants are incubated in the dark for at least 24–60 hours, more preferably for 48–60 hours.

After incubation, plant transfectants are assayed for gene expression. For example, particle transfection can be accomplished using the plasmid DNA, pFF19G, prepared according to the method described by Asano et al., *Plant Science* 79: 247 (1991), which is incorporated by reference herein in its entirety. This plasmid contains a GUS gene, whose expression is detected histochemically, according to the method of Jefferson et al., *Plant Molec. Biol. Rep.* 5: 387 (1987).

Both long-term and transient plant transfection can be measured using genetic methods described for mamallian transfectants in Examples 3 and 4, which are adapted for detecting the particular plant gene being transfected. To measure long-term efficiency of plant-particle transfection, the prototransfectants are preferably transfected with DNA molecules containing a selectable marker gene, such as NPT II, whose expression is detected by resistance to kanamycin. An example of such a DNA molecule is described by Swanson et al., *Theor. Appl. Genet.* 78:831 (1989).

The present invention is further described with reference to the following, illustrative examples.

EXAMPLE 1

Particle Transfection of COS-7 Cells
Preparation of Cells, DNA and Particles

COS-7 cells were prepared for particle transfection according to the following procedure. First, COS-7 cells were obtained from the American Type Culture Collection (Rockville, Md.) and were passaged in complete medium (RPMI 1640 median (GIBCO, Grand Island, N.Y.) supplemented with 10% fetal bovine serum (FBS)). The cells were passaged in Corning 75 cm tissue culture flasks (Corning, N.Y.), and then plated at 1 to $2 \times 10^6$ cells/plate on Falcon (Becton Dickinson, Calif.) #3003 petri dishes (100×20 mm). Plated cells were incubated for 48 hours in the media in a humidified 5% $CO_2$ atmosphere.

DNA to be transfected consisted of plasmids containing the bacterial chloramphenicol acetyl transferase (CAT) gene which were constructed using four different types of promoters including two cellular promoters, PGK-CAT and hβ-actin-CAT. PGK-CAT has the CAT gene transcribed from the murine phosphoglycerate kinase (pgk-1) promoter according to the method of Adra et al., *Gene* 60: 65 (1987), and was a donation from R. Hawley (Bayview Regional Cancer Centre, Toronto). The plasmid β-actin-CAT has the CAT gene transcribed from the human β-actin promoter described by Gunning et al., *PNAS USA* 84: 4831 (1987), and was kindly provided by A. Pawson (Mount Sinai Hospital, Toronto).

Two viral promoters, hCMV-CAT and PSV2-CAT, were also studied. hCMV-CAT was constructed using the human specific cytomegalovirus immediate early promoter (Immunex, Seattle, Wash.) to transcribe the CAT gene. PSV2-CAT has the SV40 early enhancer promoter driving the transcription of the CAT gene and was obtained from the ATCC (Rockville, Md.).

A plasmid PGK-β-gal (BlueZ) was also constructed by ligating the mouse pgk-1 promoter to a modified *E. coli* lacZ gene described by Hall et al., *J. Mol. Appl. Genet.* 2: 101 (1983), and was a gift from R. Hawley.

All plasmids were purified with two cycles of cesium chloride equilibrium density gradient centrifugation. Where indicated, plasmids were linearized with the appropriate restriction enzyme obtained from BRL (Bethesda, Md.).

Glass particles used for transfection (obtained from Sigma (St. Louis, Mo.)) were subjected to a pretreatment regimen according to McNeil et al., *J. Cell Science* 88: 669 (1987), which is incorporated by reference in its entirety, with the following modifications to the regimen. The particles were first acid-washed in two volumes of 5M HCl for 12 hours and then rinsed five times with distilled water. Particles were then alkali washed with two volumes 4M NaOH for 12 hours and then rinsed in distilled water until the pH of the wash water was 7.0. The particles were then soaked in 70% isopropanol for two hours and then rinsed with a physiologic buffer A (140 mM KCl, 10 mM HEPES (pH 7.25), 1 mM EDTA, 0.193 mM $CaCl_2$, 10 mM glucose, 1M $MgCl_2$, and 1 mM MgATP).

Particle Transfection

In performing particle transfection, the prepared cells were incubated at 37° C. for 48 hours in a humidified 5% $CO_2$ atmosphere. Cells were then washed twice with phosphate buffered saline (PBS) and further washed with buffer A (without MgATP). Where indicated, DNA (50 μg/ml) was then added to 2 ml of buffer A (with MgATP) together with 0.4 ml (approximate volume) of glass particles to petri dishes. This volume was determined to achieve the best spread of the particles over the petri dish while keeping the volume, and thus the amount of DNA required, at a minimum. The plates were then gently agitated for about 10 seconds by moving the petri dish back and forth for about one to three times to ensure even distribution of the particles. A minimal amount of manipulation was correlated with decreased cell loss.

The particles and the DNA-containing solution were washed off with 5 ml of buffer A with MgATP, 10 ml of complete media was added and the plates were returned to 37° C. Where indicated, 1 ml DNA containing (200 μg/ml) buffer A with MgATP was added to the cells and left for 10 minutes before the addition of 0.4 ml particles and 1 ml buffer. As controls, cells were exposed to DNA (at a concentration of 100 μg/ml in buffer) without the addition of particles or cells were treated with particles in the absence of DNA. Forty-eight hours later, the cells were harvested and assayed for the activity of the transfected gene.

EXAMPLE 2

Particle Transfection of Human Bone Marrow Stromal Cells

Human bone marrow stromal cells were prepared for particle transfection according to the following procedure. First, the stromal cells were obtained by several passages of the adherent layer from long term bone marrow cultures derived from aspirates of normal human donors according to Institutional Review Board approved protocols and the methods of Toneguzzo et al., *PNAS USA* 83: 3496 (1986), and Keating et al., METHODS IN MOLECULAR BIOLOGY 5: 331 (1990). Stromal cells were suitable for experiments after passaging 4–5 times in long term marrow culture medium (McCoy's 5A medium supplemented with 12.5% fetal bovine serum, 12.5% horse serum, 1% each of glutamine, sodium pyruvate, sodium bicarbonate, and vitamins, 0.8% essential amino acids, 0.4% nonessential amino acids (all from GIBCO, Grand Island, N.Y.) and $10^{-6}$M hydrocortisone (Sigma, St. Louis, Mo.)).

Plasmids containing the neomycin phosphotransferase gene (NEO), hCMV-NEO were obtained from Immunex Corporation (Seattle, Wash.) and were constructed using the human specific cytomegalovirus immediate early promoter. PGK-NEO contains the neomycin resistance gene transcribed from murine pgk-1 promoter described by Adra et al., *Gene* 60: 65 (1987), and was a donation from R. Hawley (Bayview Regional Cancer Centre, Toronto). The plasmids were purified with two cycles of cesium chloride equilibrium density gradient centrifugation. Where indicated, plasmids were linearized with the appropriate restriction enzyme obtained from BRL (Bethesda, Md.).

Suitable tissue culture flasks and petri dishes as described in Example 1 were used to passage, and to plate cells at $2\times10^6$ cells/petri dish. Cells were incubated in media for 72 hours at 37° C. in a humidified 5% $CO_2$ atmosphere, and the particle transfection procedure outlined in Example 1 was performed.

EXAMPLE 3

Assays for Transient and Stable Expression in Particle Transfected Cell Lines

Transient Expression

CAT activity in COS cells transfected according to Example 1 was assessed by first incubating cells in 1 ml of a 0.25% trypsin/PBS solution at 37° C. for 5 minutes to remove them from the tissue culture dish. The cells were then washed twice in PBS and then resuspended in 0.25M Tris. This mixture was sonicated twice for 30 seconds, diluted with an equal volume of de-ionized water and then sonicated twice for 30 seconds. This cell lysate was then centrifuged for 10 minutes in an Eppendorf microcentrifuge. The supernatant was then heated to 65° C. for 10 minutes, and assayed for CAT activity according to Neumann et al., *Biotechniques* 5: 444 (1987). Transfection efficiency was measured by the amount of radio-labelled $^{14}C$ transferred from acetyl-Co-enzyme A to chloramphenicol. As chloramphenicol is acetylated, the molecule moves from the aqueous solution into the overlying hydrophobic scintillation fluid. The rate of transfer (cpm/min) was determined over four or more time points and the average rate was determined. This was then normalized to protein concentration (cpm/min/mg protein). Protein concentration was determined using the BIO-RAD Protein Assay Reagent (Biorad, Richmond Calif.) as described by the manufacturer.

β-galactosidase activity was assessed thirty-six hours after particle transfection in COS cells (Example 1). Cells were fixed with 1% glutaraldehyde in PBS. Cells were then washed twice with PBS, and then incubated in buffer B consisting of 84 mM sodium phosphate, 2.0M KCl, 1 mM $MgCl_2$, 3 mM $K_4(Fe[CN]_6)$, 3 mM $K_3(Fe[CN]_6)$ and 0.1% Triton X-100 and 400 µg/ml X-Gal(5-bromo-4-chloro-3-indolyl-β-D-galactoside) according to the method of Takahashi et al., *Exp. Hematol.* 19: 343 (1991). Cells were then washed twice with PBS and photographed through a light microscope without removing them from the original tissue culture dish.

Long-term Expression of Transfected DNA

To establish the efficiency of long-term transfection, COS cells were particle transfected with a linearized plasmid containing the neomycin phosphotransferase gene (hCMV-NEO) or transfected in the absence of DNA. Forty-eight hours after transfection, the media in each assay dish was replaced with media containing G418 at 600 µg/ml. Stable transfection of the hCMV-NEO gene is assayed by resistance to G418 sulfate (Gibco, Grand Island, N.Y.). G418 sulfate (Gibco, Grand Island, N.Y. ) w as dissolved in complete medium to give a biologically effective concentration of 43.5 mg/ml. The concentration of G418 was increased over a period of several days to 800 µg/ml, a concentration that was lethal to all untransfected control cells. In five experiments, 37+/−19 colonies (mean±standard deviation) of G418 resistant cells were generated per plate of $2\times10^6$/cells.

To determine the frequency of clonogenic cells transformed, particle-transfected cells were cloned in 96-well plates at 0.3 to 0.5 cells per well. After 28 days of growth, the clones were exposed to 800 µg/ml G418. The number of clones resistant to G418 was obtained 14 days later. From a total of 192 wells, 15 resistant colonies were obtained. No colonies were detected from sham-transfected cells grown in G418. In contrast, 56 colonies were generated from the same number of wells inoculated with untreated cells grown in the absence of G418, indicating that the frequency of stable expression of the transferred gene is 27 percent.

In order to investigate the nature of the integrated DNA, individual NEO-resistant COS clones were grown and passaged to provide sufficient DNA for analysis. The DNA was then restriction digested and subjected to Southern analysis with a NEO-specific probe, as described below in Example 4. Results from this analysis indicated that the transferred DNA integrated within one or two sites in the host genome.

Efficiency of Particle Transfection

Gene transfer efficiency was determined to be 3.0 percent with β-galactosidase assessed in non-transformed human bone marrow stromal cells and COS cells. Long-term stable expression with the selectable marker, neomycin phosphotransferase was demonstrated in COS cells at a frequency of 27 percent (as described above).

EXAMPLE 4

Genetic Confirmation of Transfection

Isolation of Genomic DNA

Genomic DNA of particle transfectants was extracted in a solution of 150 mM NaCl, 10 mM EDTA, 10 mM Tris-HCl (pH 7.5), 0.5% SDS. The mixture was incubated for 10 m at 65° C. Proteinase K (Sigma, St. Louis, Mo.) was then added at a concentration of 10 µg/ml and the mixture was incubated at 37° C. The DNA was then extracted sequentially with phenol, phenol-chloroform and chloroform, and then precipitated with one-tenth volume of 3M sodium acetate and 2.5 volumes of ethanol as described in Sambrook et al., *MOLECULAR CLONING: A LABORATORY MANUAL*, Cold Spring Harbor (1989).

Preparation of Southern Blots

DNA was digested with restriction endonucleases (BRL, Bethesda, Md.) and separated by passage through a 1% agarose gel in a Tris-acetate buffer. The DNA was then transferred to a nylon membrane (Hybond-N, Amersham, Oakville, Ontario), prehybridized and hybridized according the method of Toneguzzo and Keating, *PNAS USA* 83: 3496 (1986). Radiolabelled probe for use in the hybridization was a randomly primed 1.3 kb Bgl II-Nru I fragment of the NEO gene as described by Feinberg et al., Anal. Biochem. 137: 266 (1983).

EXAMPLE 5

Effect of DNA Concentration of Transfection

Experimental results of particle transfection of COS cells using linearized hCMV-CAT plasmid (Example 1) demonstrate that increasing the concentration of polynucleotide molecule increases transfection efficiency. A preferred concentration, 50 µg/ml, provides a high transfection efficiency combined with requiring a lower amount of DNA, as is shown in Table 1. In these experiments, CAT activity was measured in cpm/min and normalized to mg protein. The data is presented as a mean of 3 experiments (+/–SD, n=number of experiments).

TABLE 1

EFFECT OF DNA CONCENTRATION
ON CAT EXPRESSION IN TRANSIENT ASSAYS

| Concentration of DNA | CAT activity/ng | Relative Activity |
|---|---|---|
| 25 µg/ml (n = 3) | 18 +/– 4.0 | 0.5 |
| 50 µg/ml (n = 3) | 36 +/– 3.2 | 1.0 |
| 100 µg/ml (n = 3) | 28.9 +/– 10.1 | 0.8 |

EXAMPLE 6

Effect of DNA Conformation on CAT Expression

Particle transfection with plasmid hCMV-CAT was performed on COS cells and human passaged stromal cells as described in Examples 1 and 2 to compare the effects of DNA conformation on transfection.

In these experiments, CAT activity is measured in cpm/min and is normalized to mg protein. Particle transfection using linearized plasmid DNA was considered optimal and other results are compared to the CAT activity obtained under those conditions. When particles were not used and a DNA containing solution was merely overlaid onto the tissue culture plates containing cells, a relative activity of less than 0.01 was obtained. (n=number of experiments). The results are demonstrated in Table 2.

TABLE 2

GENE TRANSFER OF LINEARIZED PLASMID DNA
COMPARED TO SUPERCOILED PLASMID DNA

| Cell Type | Linearized CAT activity/mg | Relative Activity | Supercoiled CAT activity/mg | Relative Activity |
|---|---|---|---|---|
| COS particle transfection (n = 3) | 3667.1 +/– 827.6 | 1.0 | 2388 +/– 966 | 0.65 |
| Marrow stromal cells particle transfection (n = 3) | 2550 +/– 566 | 1.0 | 2880 +/– 780 | 1.1 |

EXAMPLE 7

Effect of Particle Size

COS cells were transfected with linearized hCMV-CAT plasmid using particles of rounded glass ranging in diameter size from 150–425 µm (Sigma, St. Louis, Mo.) according to the method described in Example 1. CAT activity, determined over several time points, is reported in cpm/min. Neumann et al., Biotechniques 5:444 (1987). CAT activity/mg protein is the CAT activity divided by the amount of protein in the sample assayed as according to Bradford, Anal. Biochem., 72: 248 (1976). n=the number of plates assayed for each particular condition. As shown in Table 3, 425 µm particles demonstrate a high transfection efficiency.

TABLE 3

DIFFERENT SIZES OF PARTICLES

| Size of particles | CAT activity/mg protein | Relative Activity |
|---|---|---|
| 150µ (n = 3) | 370.5 +/– 76.5 | 0.32 |
| 212µ (n = 3) | 656.2 +/– 121.5 | 0.56 |
| 425µ (n = 3) | 1163 +/– 955 | 1.0 |

EXAMPLE 8

A Comparison of Particle Transfection Using Two Different Cell Types

Linearized hCMV-CAT plasmid DNA at a concentration of 50 µg/ml was used to particle transfect both stromal cells and COS cells. Both types of transfected cells were plated at $2 \times 10^6$/plate 48 or 72 hours prior to transfection as described in Example 1. n=the number of experiments. The results are demonstrated in Table 4 below.

TABLE 4

EFFECT OF CELL TYPE

| | CAT ACTIVITY/mg protein |
|---|---|
| COS cells (n = 7) | 56.9 +/– 20.8 |
| Stromal cells (n = 6) | 32.7 +/– 10.4 |

EXAMPLE 9

Particle Transfection with Serially-Transferred Polynucleotide Molecule Supernatant Studies have demonstrated that a very small amount of exogenous DNA enters the cells during particle transfection. When radiolabelled linearized plasmid DNA ($7.0 \times 10^4$ cpm per 100 µg DNA per assay dish) was transfected, counts remaining in the cell pellet were determined by passing the cells through a corn oil-diphenyl phthalate solution at two and six hours after transfection. At both two and six hours incubation, less than 1% of radio-labelled DNA was associated with the cell pellet, indicating that a very small amount of DNA enters the cells.

Because very little DNA is lost during transfection, particle transfection with serial DNA/buffer supernatants from prior transfection experiments is feasible. For the experiments in which DNA was transferred to a subsequent plate (recycled), the initial plate of cells was transfected and the DNA-containing buffer (primary supernatant) was removed before the particles were washed off. This buffer (secondary supernatant) was then used to transfect subsequent plates of cells.

Table 5 demonstrates that DNA-buffer can be reused successively for particle transfection of COS or marrow stromal cells. Transfer of supernatant protocol was performed three times and CAT activity shown is representative of an average±standard deviation.

TABLE 5

SERIAL TRANSFER OF POLYNUCLEOTIDE MOLECULE SUPERNATANT

| | Number of Experiments | PRIMARY CAT activity/ mg | SECONDARY CAT activity/ mg | TERTIARY CAT activity/ mg |
|---|---|---|---|---|
| COS cells: | 7 | 126.5 ± 54.5 | 96.4 ± 43.4 | 82.7 ± 21.5 |
| Passaged Stromal cells | 1 | 66.9 | 50.9 | 35.6 |

EXAMPLE 10

A Comparison: Particle Transfection Versus Transfection by Electroporation

Approximately $25 \times 10^6$ cells were used for each electroporation experiment. Cells were resuspended in 0.4 ml of PBS according to the method of Toneguzzo et al, (1988), and Toneguzzo et al., (1986) described supra. Briefly, plasmid DNA was linearized and added to cells at a concentration of 100 µg/ml and incubated on ice 10 minutes prior to transfection. A BTX 300 Electroporator (Biotechnologies and Experimental Research Inc., San Diego, Calif.) was set to discharge at 2.2 kV with a capacitance of 1000 µF. This provided a field strength of approximately 3.0 kV/cm and an effective pulse length of 14 ms. After electroporation, cells were incubated on ice for 10 minutes, and then an equal volume of media was added. The cells were then incubated for four hours at 37° C. These cells were then plated at $2 \times 10^6$ cells/plate (normalized to mg/protein) and incubated for 24 to 72 hours.

Values shown in Table 6 represent the transient expressions of CAT activity adjusted to the number of cells targeted for gene transfer ($2 \times 10^6$ cells) in each transfection. CAT activity is expressed as cpm/min/$2 \times 10^6$ cells. Values are the mean of 3 experiments (±standard deviation), except where indicated and a range is given. For the purposes of comparison, results obtained from particle transfection using linearized plasmid DNA according to Example 1 are considered as 1.0, and other values are compared to that value.

TABLE 6

A COMPARISON OF PARTICLE TRANSFECTION, DEAE-DEXTRAN AND ELECTROPORATION

| | CAT Activity | Relative CAT Activity | *P Value |
|---|---|---|---|
| Particle Transfection | | | |
| linearized DNA | 483.1 ± 15.8 | 1.0 | |
| supercoiled DNA | 392.3 ± 2.5 | 0.81 | |
| DEAE-Dextran | | | |
| linearized DNA | 302.1 ± 42.6 | 0.62 | 0.01 |
| supercoiled DNA | 409.9 ± 28.8 | 0.85 | |
| Electroporation | | | |
| linearized DNA | 419.3 ± 99.2 | 0.86 | 0.45 |
| supercoiled DNA | 310.0 ± 181.2 | 0.64 | |

EXAMPLE 11

Transfection by DRAE Dextran Method

DEAE-dextran (MW 500,000) was purchased from Pharmacia (Uppsala, Sweden). Cells were seeded at $2 \times 10^6$ per plate (Falcon 1003) and left for 48 hours in a humidified 5% $CO_2$ atmosphere. The cells were then transformed according to Holter et al. (1989) with the following modifications. COS cells transfected with hCMV-CAT plasmids were washed twice with prewarmed PBS and then incubated in 2 ml of complete media which also contained 500 µg/ml DEAE dextran and 2 µg/ml linearized, or where indicated, supercoiled plasmid DNA for 30 minutes at 37° C. Twenty ml of fresh media which contained 100 µM chloroquine was added and cells were incubated at 37° C. for 3 hours. The media was then removed and replaced with 10 ml of fresh media containing 10% DMSO and the cells were then incubated at 20° C. for 2.5 minutes. This media was aspirated and finally replaced with 10 ml of fresh media. The cells were then incubated for 48 hours before they were assayed for CAT activity For the purposes of comparison, results obtained from particle transfection using linearized plasmid DNA according to Example 1 are considered as 1.0, and other values are compared to that value.

EXAMPLE 12

Effect of Promoters on CAT Expression

The efficacy of different promoters on the expression of CAT in COS cells was investigated. Four different plasmids were particle transfected, including hCMV-CAT, PSV2-CAT, mPGK-CAT and hβ-actin-CAT, using the method described in Example 1. In duplicate experiments, hCMV-CAT was the most active, while relative activities obtained with PSV2-CAT and hβ-actin-CAT in the same cells were 0.15 and 0.02, respectively. No activity was detected using mPGK-CAT in particle transfection experiments with COS cells.

What is claimed is:

1. A kit for use in transfecting a polynucleotide molecule into non-adherent cells, comprising
   a first receptacle containing a preparation of a first antibody having specificity for an antigen of a non-adherent cell to be transfected,
   a second receptacle containing a preparation of a second antibody that can bind both said first antibody and to a support, and
   a third receptacle containing a quantity of sterilized particles for use in transfecting non-adherent cells when said non-adherent cells are immobilized to a support by means of said second and first antibodies.

2. A method for transfecting a polynucleotide molecule into a mammalian cell, comprising the steps of
   (a) contacting non-adherent mammalian cells with a first ligand that binds an antigen present on the surface of said non-adherent cell, wherein said ligand is immobilized on a support directly or is capable of being immobilized to said support indirectly by a second ligand, such that between about 0.5 and 10 million of said mammalian cells are immobilized in a viable state upon said support by at least said first ligand; then
   (b) bringing said mammalian cells into contact with liquid medium that contains particles and a polynucleotide molecule; and thereafter
   (c) agitating said medium to effect an even distribution of said particles over said cells without decreasing viability of said cells, such that at least some of said cells are transfected with said polynucleotide molecule.

3. The method according to claim 2, further comprising a step of detecting transfected cells that express said polynucleotide molecule.

4. The method according to claim 3, further comprising, prior to step (b), a step of washing said cells immobilized in a viable state upon said support with buffer A and then removing said buffer.

5. The method according to claim 2, wherein said liquid medium is buffer A containing MgATP.

6. The method according to claim 5, wherein said polynucleotide is present in said liquid medium at 25–100 µg/ml.

7. The method according to claim 2, wherein the size of each of said particles is about 300–500 µm.

8. The method according to claim 7, wherein said size of each of said particles is about 425 µm.

9. The method according to claim 2, wherein said agitating of step (c) comprises tilting said support from side to side three times.

10. The method according to claim 7, wherein said cells in step (a) are immobilized on a support indirectly by a second ligand that is (i) bound to a support and (ii) binds said first ligand with sufficient affinity to adhere the first ligand to a support.

11. The method according to claim 10, wherein each of said first ligand and said second ligand is a monoclonal antibody.

12. The method according to claim 7, wherein said first ligand is a monoclonal antibody.

13. The method according to claim 12, wherein said first antibody is a human anti-CD34+ cell monoclonal antibody and said second antibody is an anti-human antibody.

* * * * *